(12) United States Patent
Bottwein et al.

(10) Patent No.: US 6,534,017 B1
(45) Date of Patent: Mar. 18, 2003

(54) TEST ELEMENT STORAGE DEVICE

(75) Inventors: Gunter Bottwein, Lampertheim; Reinhard Bär, Mannheim; Hans List, Hesseneck-Kailbach; Friedrich Heid, Altrip, all of (DE)

(73) Assignee: Roche Diagnostics GmbH (DE)

( * ) Notice: Subject to any disclaimer, the term of this patent is extended or adjusted under 35 U.S.C. 154(b) by 0 days.

(21) Appl. No.: 09/402,315

(22) PCT Filed: Apr. 9, 1998

(86) PCT No.: PCT/EP98/02065
§ 371 (c)(1), (2), (4) Date: May 26, 2000

(87) PCT Pub. No.: WO98/47007
PCT Pub. Date: Oct. 22, 1998

(30) Foreign Application Priority Data

Apr. 11, 1997 (DE) .......................... 197 15 031

(51) Int. Cl.$^7$ .................................. B01L 9/00
(52) U.S. Cl. ................... 422/104; 422/63; 422/64; 422/58; 422/61; 422/99
(58) Field of Search ............. 422/63, 64, 99, 422/58, 61, 104; 436/46, 43, 47, 48; 206/204; 221/135

(56) References Cited

U.S. PATENT DOCUMENTS

| 3,802,842 A | 4/1974 | Lange et al. | |
| 3,853,711 A | * 12/1974 | Heden | |
| 3,918,910 A | 11/1975 | Soya et al. | |
| 4,142,863 A | 3/1979 | Covington et al. | ........... 422/63 |
| 4,218,421 A | 8/1980 | Mack, Jr. et al. | ............. 422/66 |
| 4,518,565 A | 5/1985 | Boger et al. | ................... 422/58 |
| 4,796,744 A | 1/1989 | Sanger | |
| 4,834,234 A | * 5/1989 | Sacherer et al. | |
| 4,855,109 A | 8/1989 | Muraishi et al. | ............... 422/63 |
| 4,911,344 A | 3/1990 | Kahler | |
| 5,102,624 A | 4/1992 | Muraishi | ..................... 422/64 |
| 5,154,889 A | 10/1992 | Muraishi | ..................... 422/65 |
| 5,298,425 A | 3/1994 | Kuhn et al. | .................... 436/43 |
| 5,460,968 A | * 10/1995 | Yoshida et al. | |
| 5,686,047 A | * 11/1997 | Augstein | |
| 5,757,666 A | 5/1998 | Schreiber et al. | ........... 364/509 |
| 5,846,490 A | * 12/1998 | Yokota et al. | |

FOREIGN PATENT DOCUMENTS

| EP | 0064691 B1 | 11/1982 |
| EP | 0255675 A2 | 2/1988 |
| EP | 0621481 A2 | 10/1994 |
| EP | 0654668 A1 | 5/1995 |
| FR | 1438418 | 7/1966 |

* cited by examiner

Primary Examiner—Ana Fortuna
(74) Attorney, Agent, or Firm—Richard T. Knauer; Roche Diagnostics Corporation

(57) ABSTRACT

The invention concerns a magazine for storing test elements (1) with one or several test zones (3) which are attached adjacent to one another on a rectangular support, wherein the magazine has at least one pair of guide grooves (18a, b) located opposite to one another into which the test elements are inserted in such a way that they lie directly adjacent to one another and the edges of adjacent supports abut one another. A further subject matter of the invention is a system which comprises a slide (14, 31) in addition to the magazine according to the invention which is used to push a layer of test elements along the guide grooves towards the opposite end of the layer to remove test elements from the magazine.

16 Claims, 12 Drawing Sheets

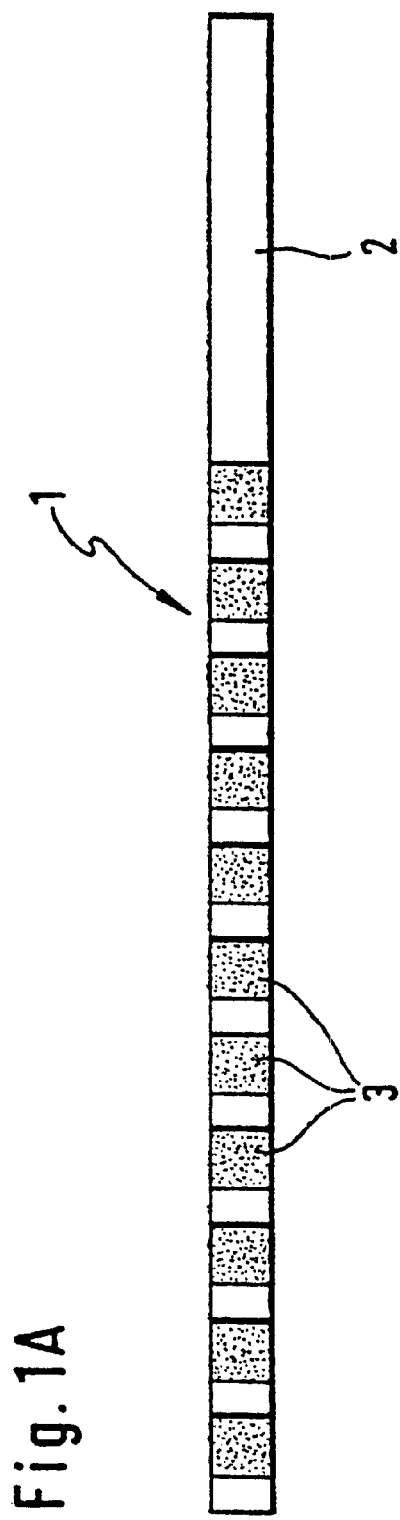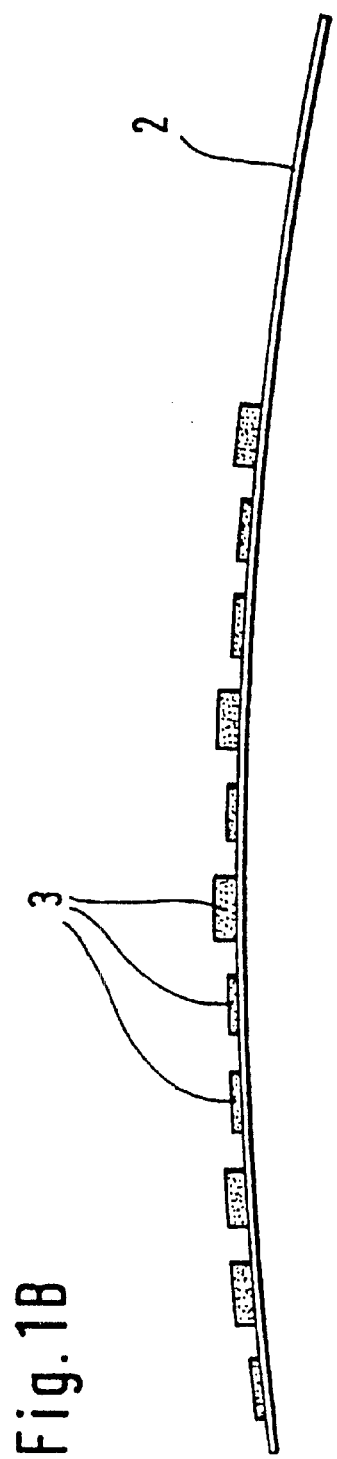

Figure 4:
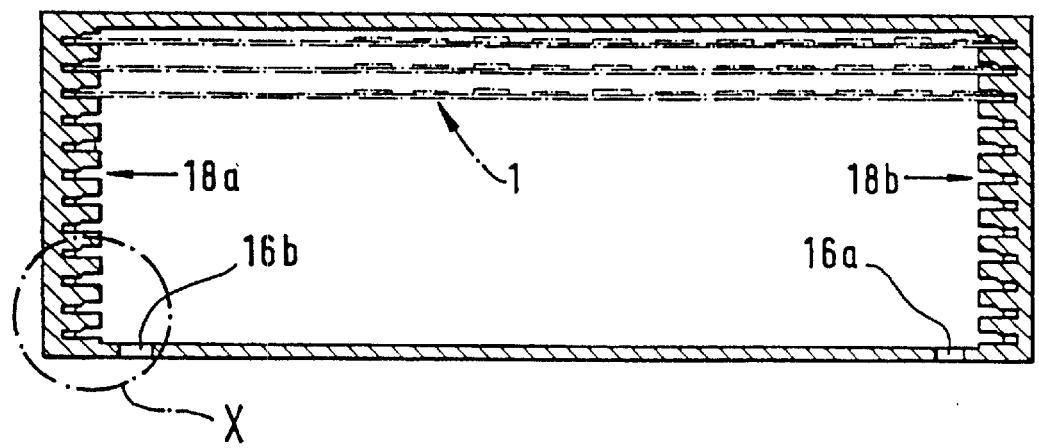

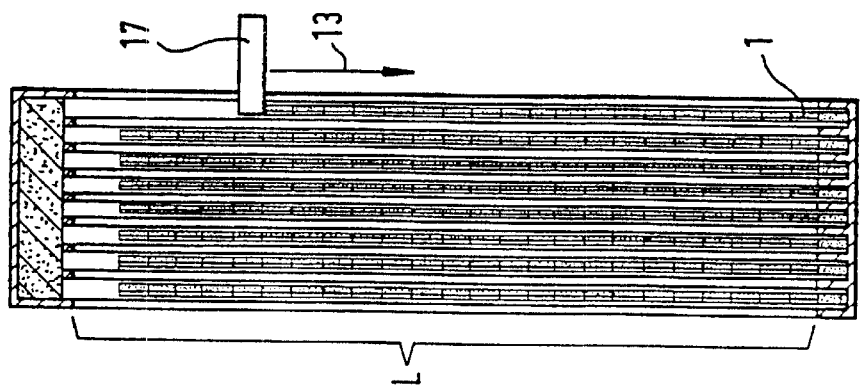
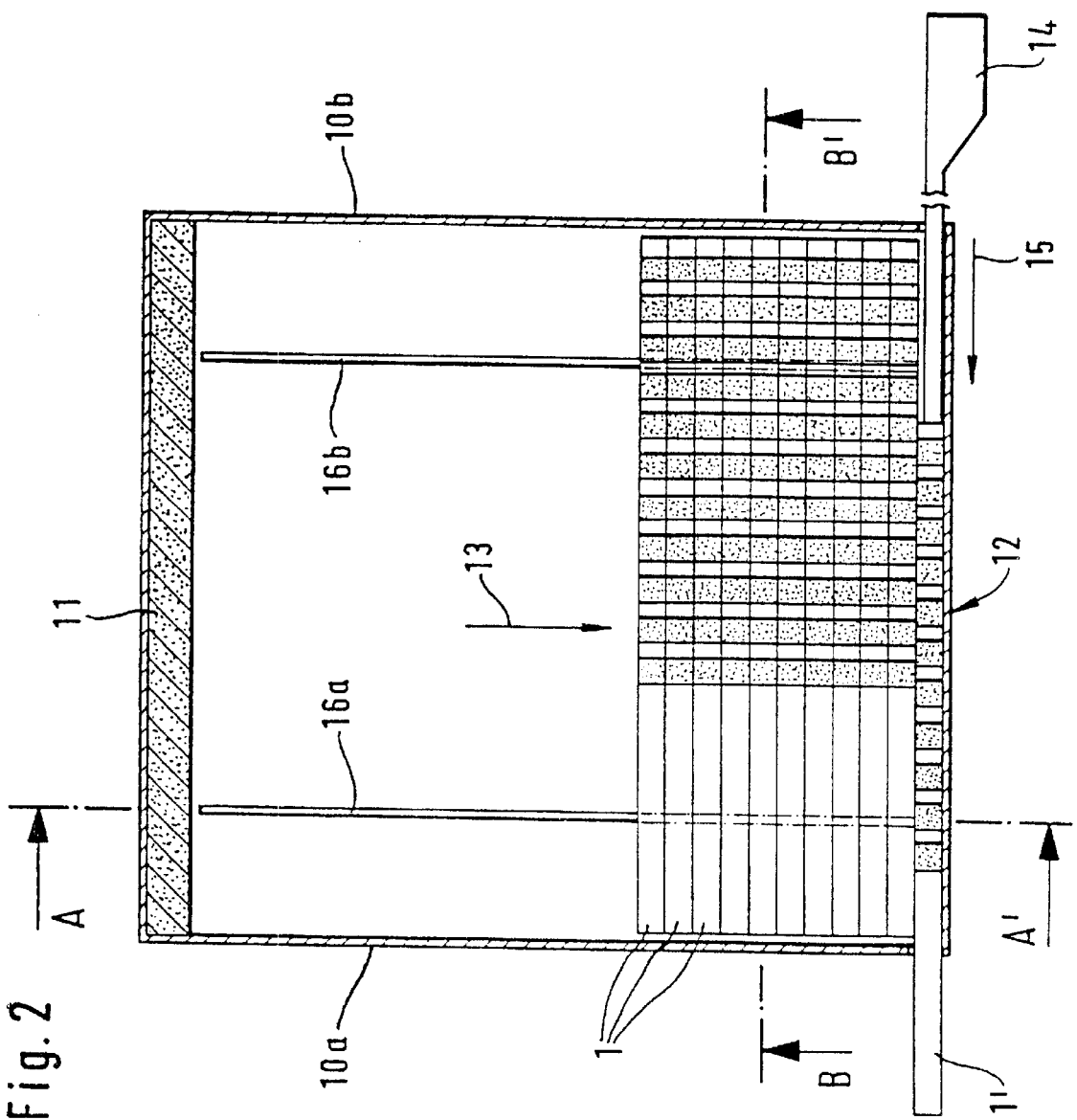

Prior Art

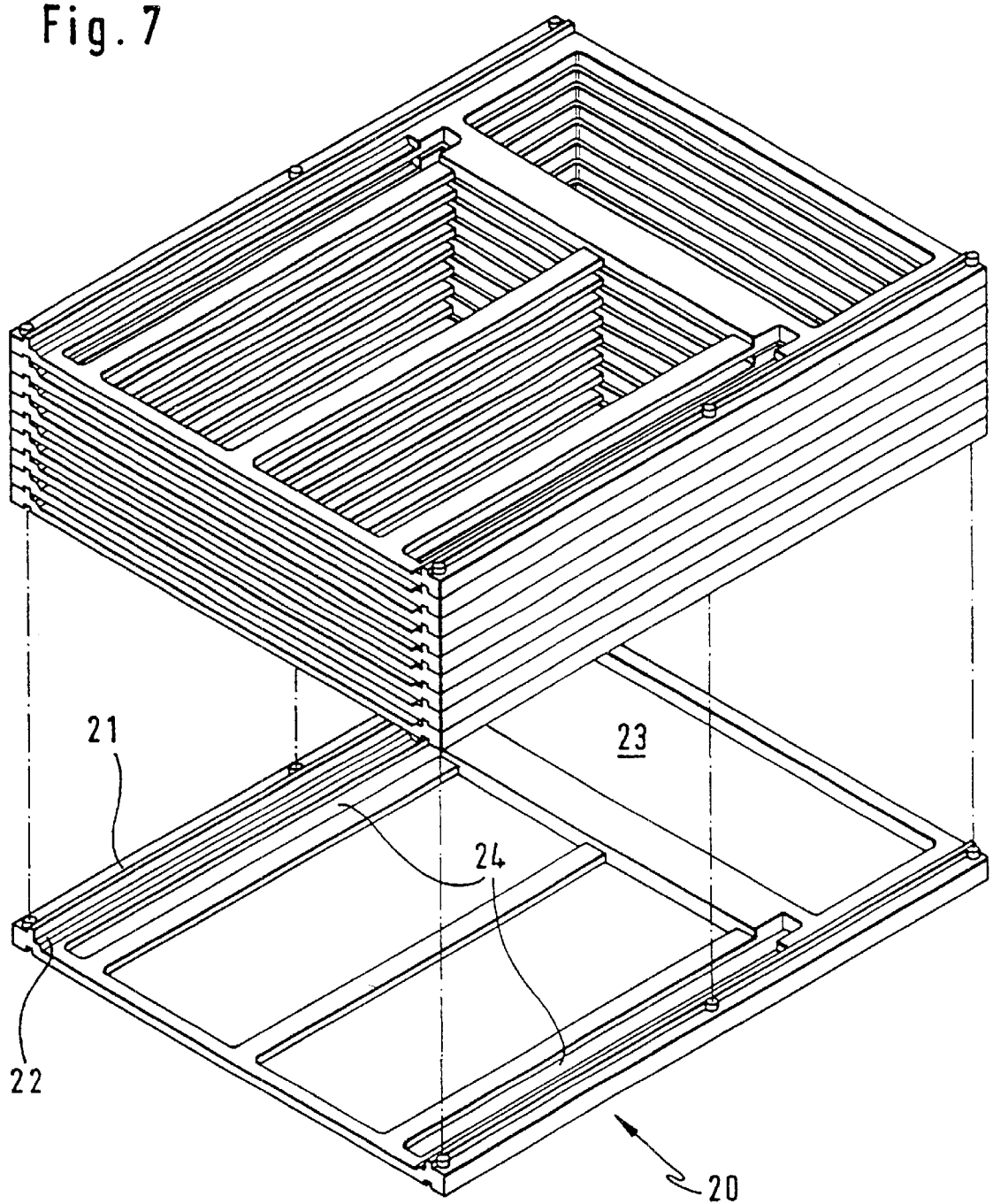

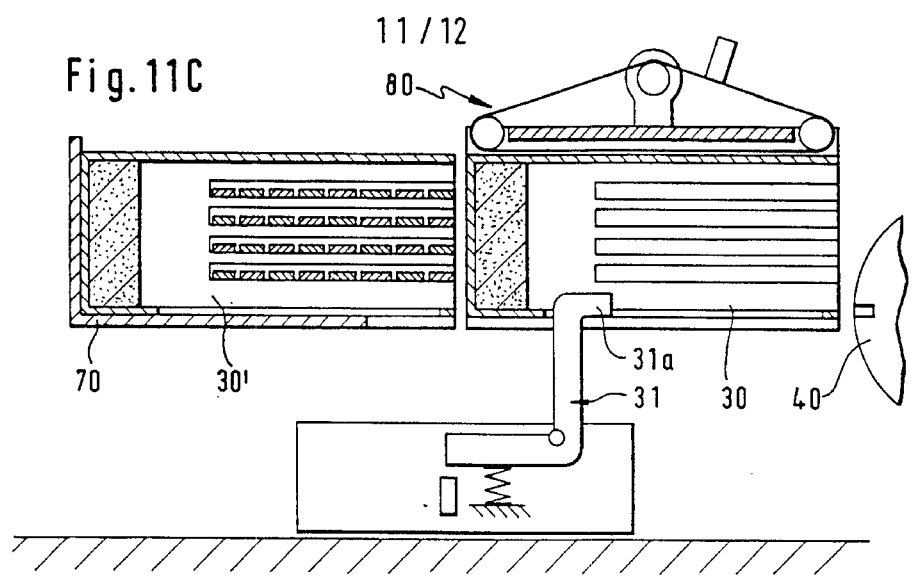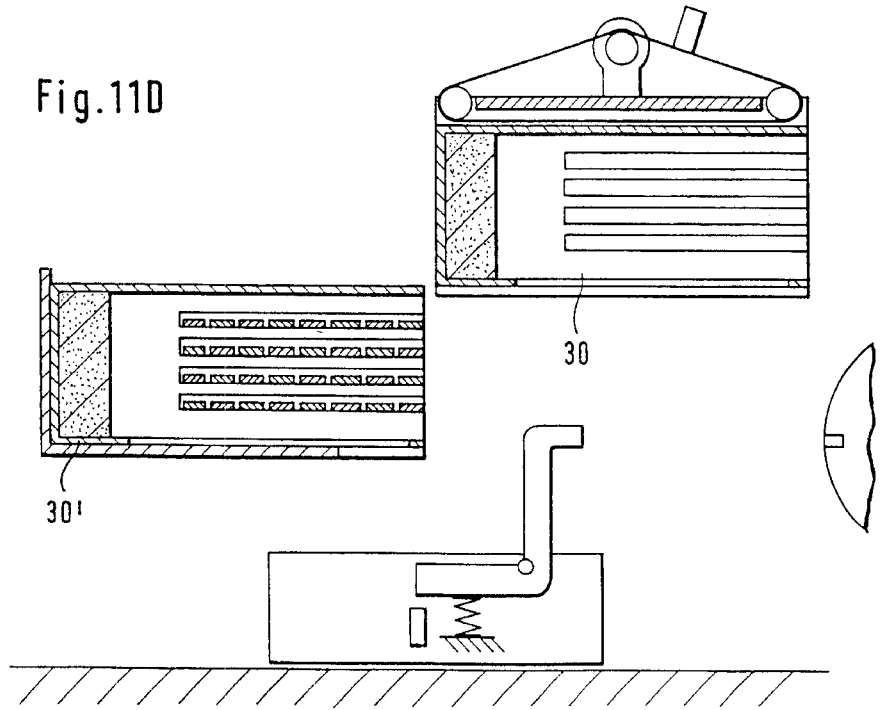

TEST ELEMENT STORAGE DEVICE

The field of the present invention is the storage of test elements such as those used to detect analytes in sample liquids. Such test elements are used especially in the field of urine analysis and in the field of blood sugar determination. In addition test elements are widely used in environmental analysis. Another field of increasing importance relates to immunological tests e.g. the detection of drugs, HCG and HIV in blood and urine.

The test element is contacted with a sample in order to detect an analyte or to analyse a sample liquid. In this process a surface can for example be rubbed with the test element. However, the usual field of application for test elements is to analyse sample liquids whereby the sample liquid is either applied to the test element (especially for determinations from blood, serum, liquor) or the test element is dipped into the sample liquid (in particular urine).

Most test elements have to be protected against moisture to avoid reagent decomposition. This applies equally to so-called optical test strips in which a colour change is caused by reaction of an analyte with the sample and also to so-called sensor elements in which a chemical change of the test element caused by the sample is evaluated electrochemically. In addition it is usually necessary to protect test elements from mechanical influences and contamination in order to ensure reliable analytical results. Several types of test element storage methods are known in the prior art. In the first procedure loose test elements are present in a container such as a tube which can be sealed by a stopper or such like. It is also known that test elements can be sealed individually in water-vapour tight foils. However, with the said storage methods it is difficult to remove the test elements mechanically from the storage container or the sealing foil. A number of magazines are known in the prior art in connection with a mechanical removal of test elements as described for example in the patents U.S. Pat. Nos. 5,102,624, 5,154,889, 3,918,910, 4,911,344 and 4,142,863. In this type of magazine test elements are used which are stacked on top of one another. The test elements described in these US patents are specially adapted for use in a magazine i.e. they have a uniform thickness and can be moved relative to one another without getting caught on one another or jamming. However, the majority of commercial test elements do not have a uniform height profile and can therefore not be easily used in magazines of the prior art. A magazine is described in the specification U.S. Pat. No. 3,918,910 which is suitable for storing test elements in which several detection zones are mounted on a support. For manufacturing reasons the detection zones project over the support and thus cause a varying vertical structure of the test element. In FIGS. 5, 6, 7, 9 and 22 of U.S. Pat. No. 3,918,910 a magazine is shown which is suitable for storing such test elements. In this magazine the test elements are stacked on top of one another in such a way that the upper side and underside of successive test elements face one another. The stack of test elements is pressed by spring elements towards a region from where a test element is removed by being pushed or pulled out. Experimental investigations have shown that such magazines are very prone to malfunction. Failures occur frequently in which none of the test elements can be securely gripped by the withdrawal unit or two test elements are erroneously simultaneously transported from the magazine.

Devices are also known in the prior art for separating test strips which can be used to remove individual strips from a disordered quantity of test strips. Such a device is described for example in EP-A-0 255 675. Another separating device is disclosed in U.S. Pat. No. 5,298,425 which also describes a correction of the position of the individual test elements. Experience has shown that devices of this type are very susceptible to break down especially when the test elements are bent.

The object of the present invention was to provide a magazine which operates reliably with the widely used commercial test elements with an uneven height profile. An additional object of the present invention was to provide a magazine which enables a mechanical removal and a high packing density of the test elements.

An additional object of the present invention was to propose a system which enables an automated dispensing of test elements by interaction of a magazine and a removal device. In particular an object of the invention was to reduce the susceptibility to malfunction of known devices of the prior art for separating test elements.

The object is achieved by a magazine for storing test elements which has at least one pair of opposite guide grooves into which the test elements are inserted so that they lie directly adjacent to one another and the edges of adjacent test elements abut one another.

The present invention also concerns a system for dispensing test elements having a magazine with at least two opposite guide grooves into which the test elements are inserted so that they adjoin one another in one plane and the edges of adjacent test elements abut one another and containing a slide one end of which engages the layer formed by the test elements and moves the test elements along the grooves towards the opposite end of the layer.

Figure 5:
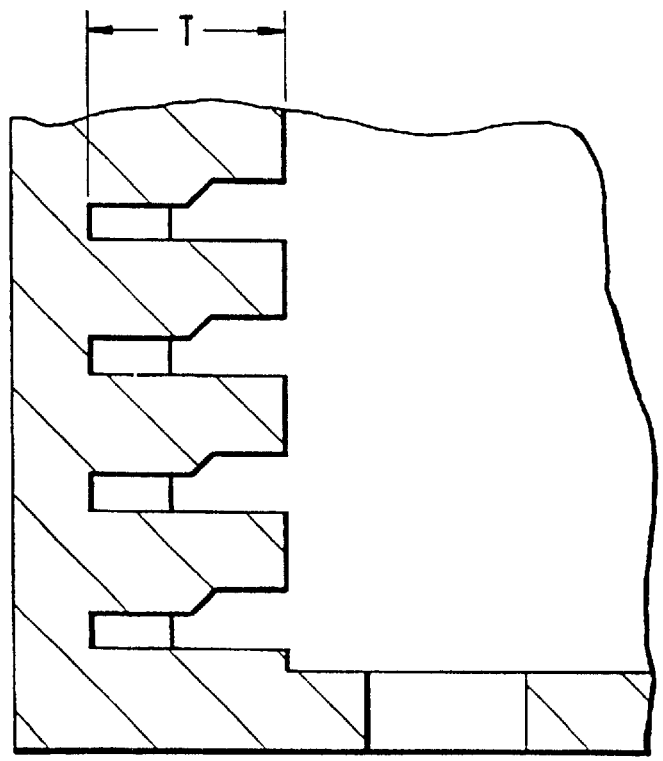

Within the scope of the present invention it was found that the problems associated with a magazine according to U.S. Pat. No. 3,918,910 are mainly due to tilting of the test elements. With reference to FIG. 5 of U.S. Pat. No. 3,918,910 (see FIG. 6 of this application) this means that the test elements get into a sloping position relative to the plate (61) or even the plate (61) itself can become lop-sided. This problem was observed in particular when the various test zones of an individual test element have a different height which is frequently the case for commercial test elements with several detection zones. It was also found that the flexibility of the test elements allows bending or even twisting of the test elements so that it is difficult to securely grasp such a test element with a mechanical device. The present invention therefore proposes a magazine in which the test elements are guided in guide grooves and are arranged such that the edges of adjacent test elements directly abut one another. The present invention utilizes the fact that as a result of their manufacture the test elements have an accurately defined width which is constant over the length of the test strip. If, as intended by the invention, both ends of the test elements are guided in grooves and the test elements are arranged next to one another instead of above one another as in the prior art, then as a rule the test elements, but at least the two ends of the test elements, can be definitely positioned. Accordingly the present invention allows a reliable mechanical removal of test elements from the magazine. In particular the magazine of the present invention is suitable for storing test elements which are flexible and/or have an irregular height profile. The present application additionally describes a system which enables test elements to be removed from the magazine according to the invention.

Commercial test elements are shown in FIGS. 1A and 1B of the present application. FIG. 1A shows a top-view of a test element. The test element (1) has a support (2) on which several test zones (3) are applied. The rectangular test element shown has a shorter side which is named width in the following and a longer side which is named length. FIG. 1B shows a side-view of a test element. The different heights of the test zones (3) and a bending of the test element can be clearly seen. The bending of the test element can be due to the properties of the support (2) as well as due to the manner in which the test zones (3) are applied. In a particularly advantageous manufacturing method for test elements, the test zones are mounted on the support and subsequently covered with a fine net. This procedure is for example described in U.S. Pat. No. 3,802,842. The intrinsic tendency of the net to pull together causes a bending of the test element. In addition the bending may be caused by the support material. Plastic foils are preferably used as support materials which are cut into small strips during manufacture of the test elements. Hence a curvature of the foil can also lead to a curvature of the test element.

A magazine according to the invention for the storage of test elements has at least one pair of opposite guide grooves into which the test elements to be stored are inserted. The guide grooves guide each of the two opposite ends of a test element. If several test elements are inserted successively into a guide groove, then the test elements come to lie side by side and the longitudinal edges of the supports of adjacent test elements touch one another. The distance between the opposite guide grooves is selected according to the length of the test elements. The distance between the bottoms of the grooves (the regions of the grooves that are furthest apart) preferably corresponds to the length of a stretched test element. The depth of the grooves and the spacing of the grooves is determined by the length of the test element section which is guided by the groove. If the distance between the grooves at their deepest point corresponds to the length of the test elements, then the guided length of the test elements equals the depth of the grooves. However, if the grooves are far apart, then there is play of the test elements in their longitudinal direction and the guided length corresponds to the depth of the grooves minus this play. A slight play of the test elements in their longitudinal direction has proven to be advantageous for a satisfactory functioning of the magazine. This play is advantageously 0.5 to 20% of the test element length. It has turned out to be usually sufficient to guide 0.3 cm of the length of the test element. The test element sections which are guided by the grooves are preferably 0.4 to 1.0 cm long. However, the invention also intends to encompass those embodiments in which the two grooves are each so deep that they receive one half of the test strip and the grooves are additionally connected together in such a way that a continuous slit is formed. In the scope of this invention such a slit is understood as a special form of a groove pair. Such a slit for guiding test elements is advantageous since it can be used to suppress the bending of the test elements since the test elements are guided over their complete length. However, for manufacturing reasons magazine designs are more advantageous in which the grooves have a depth of less than 2 cm.

The length of the grooves determines the number of test elements which can be held. There are hardly any limitations to the length of the grooves. However, groove lengths between 5 and 15 cm are favourable since they result in compact magazines that are easy to handle. If slits (instead of grooves) are used to hold the test elements their length is essentially technically limited by the tools since it is difficult to provide shaping tools for large slit lengths for example above 10 cm. However, this difficulty does not apply to the use of grooves and there are hardly limitations in the groove length. In both cases i.e. when using grooves or slits it must be ensured that the grooves or the slit ends are essentially parallel in order to avoid the test elements jamming or falling out.

It is advantageous according to the invention when the magazine has pairs of guide grooves arranged above one another so that test elements can be stored in layers arranged above one another which increases the holding capacity of the magazine. It has proven to be particularly favourable for handling if a magazine has 8 to 15 layers of test elements. For the storage of 300 test elements it is for example advantageous to use a magazine with 12 layers whereby 25 test elements are located in each layer.

It has already been mentioned that in addition to ordering and dispensing test elements, the magazine can also have the function of protecting the test elements from moisture and mechanical influence. Hence the magazine can have walls which close off the interior from the outer space. The magazine must have one or several openings to remove test elements. These openings can be closed by a mechanical closure such as a hinged cover or a bonded sealing foil. In addition it is advantageous to seal the entire magazine, even if it is closed, in a water-vapour tight external packaging for transport.

In a preferred embodiment of the magazine the guide grooves are integrated into the side walls of the magazine. In addition these side walls can already be connected together during the production process by additional walls in particular an upper and lower wall. Such arrangements can be preferably manufactured as one piece. The injection moulding process is particularly suitable for this. However, it may be technically simpler with regard to tools to individually form the walls of the magazine (preferably in an injection moulding process). Since the grooves of one side of the magazine are formed by one half of the tool, the individual grooves have only very small tolerances relative to one another. If the parts of the magazine are individually formed then the side walls, upper and underside, front and rear side are advantageously each identical so that the same tools can be used.

However, it is also advantageous to individually form the walls in an injection moulding process such that they are connected together by film hinges. Such a structure (folded box) can be converted into a magazine after the moulding by locking together the individual walls.

In a further embodiment the cassette is assembled from n+1 injection moulded parts whereby n is the number of strip layers. All parts are identical (repeat parts). They are flat frames which can be released from the mould in an injection moulding process without a slide. If these are assembled (clipped, welded by ultrasound or glued) with the flat sides facing each other, then two pieces in each case form the opposite grooves for a layer of strips. It is advantageous for the frames to have two recesses. The smaller recess of the frame forms a cell which is open at the top and bottom in which a bag of desiccant can be placed. This can for example be prevented from falling out by a paper tape.

The width of the groove and thus the spacing of the layers of strips is slightly less precise in this embodiment due to the effects of the joint tolerances.

As already mentioned it is necessary that the magazine has openings to remove test elements. It has proven to be advantageous to integrate one or several openings into a side wall of the magazine. Such an opening is at the level of a groove so that a test element which is located in the groove adjacent to the opening can be removed from the magazine by displacement along its longitudinal axis. For this purpose the opening preferably has a rectangular cross-section the height of which is about 10 to 50% larger than the maximum height of the test elements and the width of which is about 10 to 50% larger than the width of the test elements. If several pairs of grooves are used in a magazine, each pair of grooves preferably has one such removal opening. In addition it is advantageous for each of the groove pairs to have an additional opening in the opposite side wall through which a slide can penetrate into the magazine in order to push out a test element. The above-mentioned openings can be at least partially sealed by sealing foils for commercial magazines. These sealing foils can be removed before use. However, it is advantageous if the sealing foils are pierced by the slide or an emerging test element.

In a further particularly simple embodiment of the magazine the test elements are removed by moving the test elements beyond the end of the groove (in the longitudinal direction of the grooves) i.e. they are moved perpendicular to the longitudinal axis of the test element. In this embodiment the grooves of a pair of grooves are opened on one side so that test elements can be pushed out beyond the end of the grooves. Hence the magazine has an end face which is perpendicular to the side walls of the magazine and in which there is one opening per pair of grooves for the discharge of test elements. These discharge apertures preferably have a rectangular cross-section whose width is 10 to 30% larger than the maximum height of the test elements and whose length is 0.5 to 20% larger than the length of the test strips. In a variant of this embodiment which is particularly simple to manufacture the magazine has no end wall and the front end is merely sealed with the sealing foil to transport the magazine. The sealing foil can serve to seal the end wall against penetration by moisture. However, if the moisture protection is accomplished in another manner (e.g. by an external packaging), then the sealing foil can optionally be omitted. However, it has proven to be particularly effective to glue over the areas of the front end in which the ends of the grooves are located with a foil. In this manner the test elements are prevented from falling out and the foil can also be pierced by the test elements. A particular advantage of this embodiment is that the foil only has to be opened in the area of the layer from which they are removed. The other (still complete) layers of test elements remain protected by the foil so that no test elements can fall out of the magazine when it is tilted.

For the successive removal of test elements from the magazine it is necessary that the test elements can either be transported into a removal position or be directly ejected from the magazine. In the simplest case the magazine is designed such that the grooves are vertical and the test elements in the grooves are transported downwards by gravity. In this case a removal position is located at the lower end of the magazine or the magazine is opened so that the test elements can directly emerge from the magazine. In the latter case it is necessary that a closure is present which prevents the test elements from falling out in an uncontrolled manner and enables a successive withdrawal.

The inside of the magazine preferably contains one or several spring elements which transport the ensemble of test elements which is present in a pair of grooves together towards a removal position. Such spring elements can for example be spiral springs which are located at the end of each groove opposite to the removal position. Spring elements also stabilize the arrangement of test elements even if the magazine is not completely filled. This prevents the test elements from crossing or becoming disordered in another manner which would greatly reduce the reliability of the magazine.

In a particularly preferred embodiment of the magazine it has at least one recess in the upper side or underside through which a slide can be inserted into the magazine. Such a slide enables the transport of the test elements to be carried out from outside. The slide can be attached to the outside of the magazine so that it can be manually slid by an operator. However, the slide is preferably part of an analytical instrument which operates with test elements. In this case the slide is controlled by a drive unit which is part of the analytical instrument so that the removal of test elements can be controlled by the analytical instrument. As a result test elements are only removed from the protecting magazine when they are required by the analytical instrument.

A unit comprising a magazine and a slide which serves to remove test elements forms a system for dispensing test elements which is also a subject matter of this invention. This system includes a magazine with at least two opposite guide grooves into which the test elements are inserted such that they lie directly next to one another in one plane and the edges of adjacent test elements abut one another. The system also includes a slide which at one end engages the plane formed by the test elements and moves the test elements perpendicular to their longitudinal axis towards the opposite end of the plane. As already described the said slide preferably reaches into the magazine through a recess in a magazine wall. The recess required for this is kept as small as possible in order to minimize penetration of moisture into the magazine. The recess is preferably a slit which is parallel to the grooves in the upper or underside of the magazine. The opposing longitudinal slides of the slit can have rubber lips which rest against another in the resting position and thus largely prevent penetration of moisture. For removal a slide is inserted between the rubber lips and is slid along the slit. Due to the elastic property of the rubber lips only a relatively slight permeability through the rubber lips is formed in the area where the slide penetrates and most of the slit is adequately sealed against moisture.

In order to remove test elements the slide is moved incrementally by a length of path which essentially corresponds to the width of a test element so that the test elements are successively moved into a removal position or are directly ejected from the magazine. The drive unit for the slide can for example be a nut which is located on a threaded rod. The threaded rod can be turned by a stepping motor which in turn is controlled by a control unit. As already mentioned it is advantageous if the control unit is linked to a control unit of an analytical instrument so that the time of removal can be suitably controlled. The slide can be directly attached to the said nut for example in the form of a metal pin. A rotation of the threaded rod causes a linear thrust of the pin which is used to move the test elements.

If a magazine is used with several pairs of grooves, it is advantageous to be able to control the depth of penetration of the slide into the magazine. In an advantageous procedure the slide firstly enters the magazine to such a depth that it is located at the height of a first layer (level) of test elements and transports the ensemble of test elements located in this plane in such a way that the individual test elements successively reach a removal position. After this layer has been completely emptied, the slide moves back, the penetration depth is increased such that it is at the level of a second layer of test elements and the removal process is repeated. Further layers of test elements can be emptied in a corresponding manner.

For the successive removal of test elements from the magazine it is important that the sliding of the test elements into the removal position within the magazine and the removal of the test elements from this position takes place in a coordinated manner. The removal of test elements from the removal position can be achieved by a second slide which slides the test element located in the removal position along its longitudinal axis and thus pushes it out of the magazine. The removal can also be achieved by inserting a gripper into the magazine and pulling a test element from the removal position. Combinations of the two removal processes are also possible in which the test element is firstly partly slid along its longitudinal axis by a slide such that the test element can be more easily gripped by a handling unit.

A removal cycle for test elements comprises the following steps:

Removal of a test element from a removal position of the magazine (can take place by sliding out, pushing out or a combination of both processes)

Sliding an ensemble of test elements located in one plane so that a new test element is transported into the removal position.

Within the scope of the present invention a system is additionally described containing a magazine according to the invention and a slide for sliding layers of test strips and a roller with at least one groove into which a test element can be inserted and transported by rotating the roller. The magazine and a region of the roller are preferably located in a moisture-tight housing so that the test elements located in the magazine are not destroyed by moisture. A coordinated operation of the slide and the roller enables the test elements to be successively transported from the housing.

Figure 6:
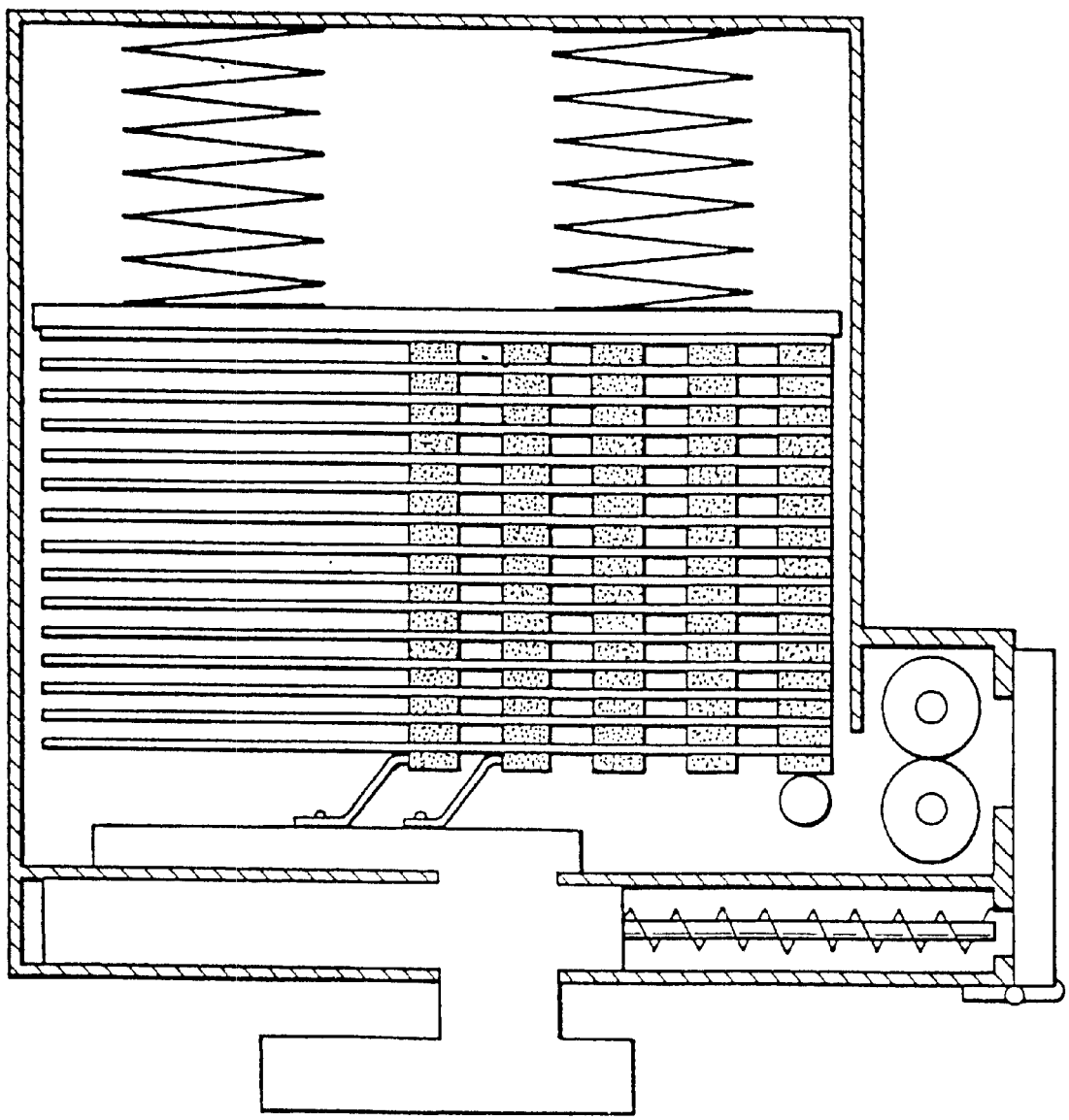

The present invention is illustrated in more detail by the following figures:

FIG. 1A: top-view of a test element
FIG. 1B: side-view of a test element
FIG. 2: section through a magazine along a plane of test elements
FIG. 3: section through a magazine along cutting line A' in FIG. 2
FIG. 4: section through a magazine along the line B' in FIG. 2
FIG. 5: cutaway enlargement of the area X in FIG. 4
FIG. 6: state of the art (U.S. Pat. No. 3,918,910)
FIG. 7: magazine constructed from assembled frames
FIGS. 8A, 8B, 8C, 8D, 8E: systems for dispensing test elements
FIG. 9: roller with groove for holding test elements
FIG. 10: system for removing test elements from the roller
FIGS. 11A, 11B, 11C, 11D, 11E, 11F: systems for dispensing test elements with refill devices FIG. 1 shows a top-view of a test element. In addition the support (2) and the test zones (3) can be seen. FIG. 1B shows a further test element in a side-view. In particular FIG.1B illustrates the different heights of the test zones (3) and the bending of the support (2).

FIG. 2 shows a magazine along a layer (plane) of test elements (1). The test elements are arranged in the magazine in the same direction and side by side. Grooves for holding test elements are located in the side walls (10a) and (10b). The rear side of the magazine has a desiccant chamber (11) which serves to absorb moisture which penetrates the magazine. Substances known in the prior art e.g. silica gel or molecular sieves can be used as desiccants. The desiccant chamber (11) closes the rear side of the magazine in such a manner that no openings remain in order to prevent moisture penetration.

FIG. 2 shows a layer of test elements which has already been half emptied. It was emptied by moving the test elements from the rear side of the magazine towards the front side (12) as indicated by the arrow (13). The test element (1') nearest to the front side is in the removal position. The test element (1') is removed by being pushed out of the magazine in the direction shown by the arrow (15) by an ejector slide (14). For this purpose the magazine has an opening in its right side surface (10b) through which the ejector slide (14) can penetrate into the magazine. The magazine also has an opening in the left side surface (10a) through which the test element (1') can emerge from the magazine.

FIG. 2 additionally shows slits (16a) and (16b) although these are located in the upper side of the magazine and are not in the plane of test elements. Slides which move the ensemble of test elements in the direction of the arrow (13) can engage in the slits (16a) and (16b).

FIG. 3 shows a section through the magazine of FIG. 2 along the line (A–A'). In FIG. 3 the slide (17) for sliding the test elements towards the removal position is shown. FIG. 3 also shows the groove length (L).

FIG. 4 shows a diagram of the magazine from FIG. 2 along the cutting line (B–B'). The pairs of grooves (18a, 18b) in which the test elements are guided can be seen in FIG. 4. Each pair of grooves contains two opposite grooves. The magazine shown in FIG. 4 has 12 such pairs of grooves so that test elements can be stored in 12 planes or layers.

FIG. 5 shows a cut-out enlargement (5-fold) of the region (X) in FIG. 4 in which the structure of the grooves used in this case can be seen more closely. The grooves shown have a depth (T) in which the ends of the test elements are inserted. FIG. 5 shows that each of the grooves has a narrower and a broader part. This is advantageous when the test zones on the support extend close to one end of the test element. In this case a groove with two regions of thickness can be advantageously used so that the extreme test element end which is not covered by a test zone can be guided in the narrower region of the groove and in addition a neighbouring region in which a test zone is located can be guided by the broader region of the groove.

The distance between the grooves shown in FIG. 5 is ca. 2 mm. Such a small spacing can be achieved despite bending of the test elements without risk of jamming of neighbouring planes of test elements. In this connection it is advantageous to arrange the test elements in the same direction in the plane so that the upper side of a test element in one layer comes to lie next to the underside of the test element in the next higher layer. Since a bending of test elements usually occurs in the same direction for each batch, the layers of test elements have the same direction of curvature and an adequate distance between the layers remains ensured.

FIG. 7 shows an exploded view of a magazine which is plugged together or clipped together from individual frames (20). In the example shown the frames are shaped such that the lateral edge (21) is raised above a ledge (22). The underside of the frame is essentially planar in the area of the edge (21) and the ledge (22) so that when two or several frames are stacked on top of one another a groove is formed by the ledge (22) and the overlying bottom surface of the next frame. The frames have a front part in which the grooves are located and a rectangular cut out (23). This forms a cavity in the assembled magazine which can be filled with a desiccant or with a desiccant container. The frames (20) can also have slits (24) (two in the example shown) into which a slide can engage to move the test elements.

FIG. 8 shows a system for dispensing test elements. FIGS. 8A to 8E show the steps for removing a test element. The system shown in FIG. 8A has a magazine (30) in which several layers of test elements are arranged edge to edge. This magazine essentially corresponds to that shown in FIG. 3. In particular the grooves of the magazine are open on the side facing away from the desiccant (60) so that test elements can be successively transported out of the magazine by sliding a layer of test elements. The underside of the magazine has one or several slit(s) into which the slide(s) (31) can engage into the magazine. One axis (32) of the slide is in turn pivotally connected to a movable sliding carriage (33). In order to remove test elements the magazine (30) is moved to a level at which a layer of test elements is positioned at the level of the front end (31a) of the slide. The slide is then moved towards the layer of test elements by operating the sliding carriage. The slide engages the layer of test elements is shown in FIG. 8A and slides the entire layer so that the test elements are moved laterally towards the opened end of the magazine. A pivoted roller is arranged opposite to the opening of the magazine which has at least one groove for holding a test element. The roller preferably has two grooves of essentially identical geometry. In order to remove a test element, the roller (40) is rotated such that the at least one groove (41) is located at the level of the layer of test strips moved by the slide. As a result of moving the slide the test element in the layer which is furthest away from the slide is pushed into the groove (41). FIG. 8B shows a state in which the said test element is already located in the groove. The test element is pushed to the end of the groove (41) by movement of the sliding carriage (33) and further movement of the sliding carriage (33) leads to a rotation of the slide (31) around its axis (32) since the layer of test elements arranged edge to edge cannot be indefinitely compressed. The slide is preferably held in its resting position by a spring (34) and a movement from the resting position by rotation around the axis is detected by a sensor (35). This sensor can for example be a light barrier whose light path is interrupted when the rear end (31b) of the slide dips. This interruption can be detected with a control device and the movement of the sliding carriage (33) towards the roller (40) can be stopped. Consequently this device can reliably and completely push a test element from the magazine into the groove without needing to know the width of the test element. Hence the device is largely independent of variations of test element width which for production reasons are virtually unavoidable. Starting with the position shown in FIG. 8B the sliding carriage is moved in the opposite direction which takes the pressure off the layer of test elements and the slide returns to its resting position with regard to rotation around the axis (32). The test element which is now located in the roller can be transported away by rotating the roller. The magazine and the part of the roller which serves to hold a test element are preferably located within a moisture-tight housing (50). This can prevent destruction of test elements located in the magazine by moisture. This is additionally ensured by a desiccant (60) which is part of the magazine. Since the groove for holding the test element can be located within the housing (50) as well as outside, special measures are required to seal the region of the roller to penetration by moisture. This can for example be achieved by rubber lips or such like which tightly rest against the roller and ensure moisture sealing when the roller is rotated. Since the groove loaded with a test element must, however, be rotated through such a rubber lip, the construction shown in FIG. 8 has proven to be more suitable for avoiding penetration by moisture. The housing (50) has protecting parts (50a, 50b) which are arranged relative to the exterior peripheral surface of the roller (40) in such a way that the roller is surrounded as tightly as possible in these areas. There are gaps between the protecting parts (50a, 50b) and the roller (40) which enable an easy rotation of the roller and ensure that also test elements which protrude above the external contour of the roller can be transported without destruction. The gap between the protecting parts and the roller represent a leakage path for moisture through which a certain amount of moisture can penetrate. However, this amount is so low that it does not lead to a rapid decomposition of the test elements.

Figure 8A:
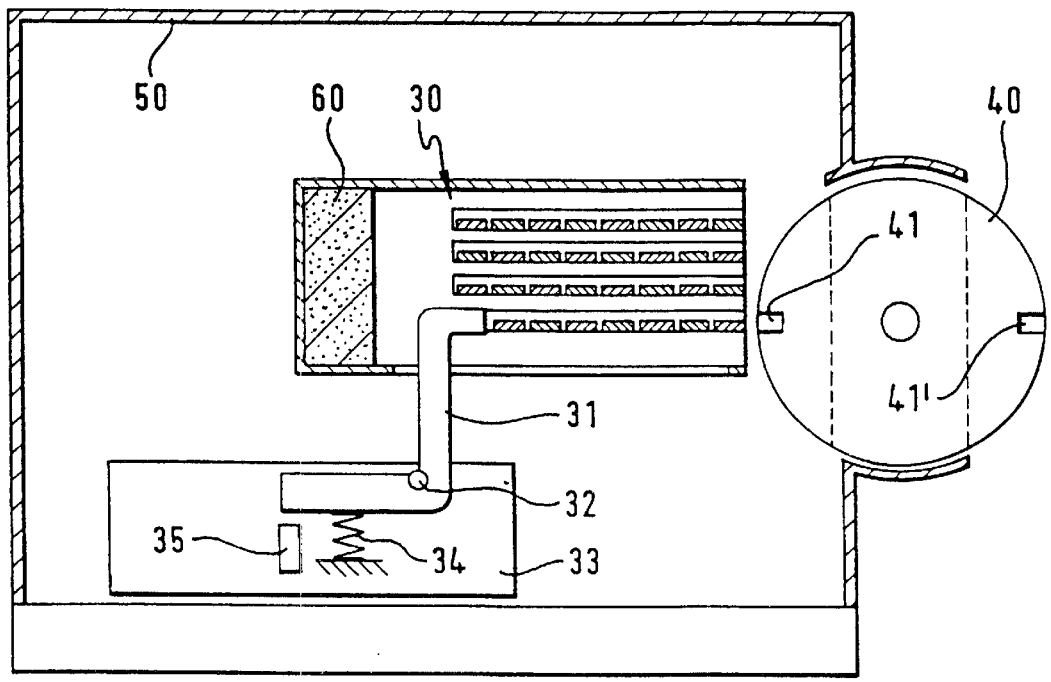
Figure 8B:
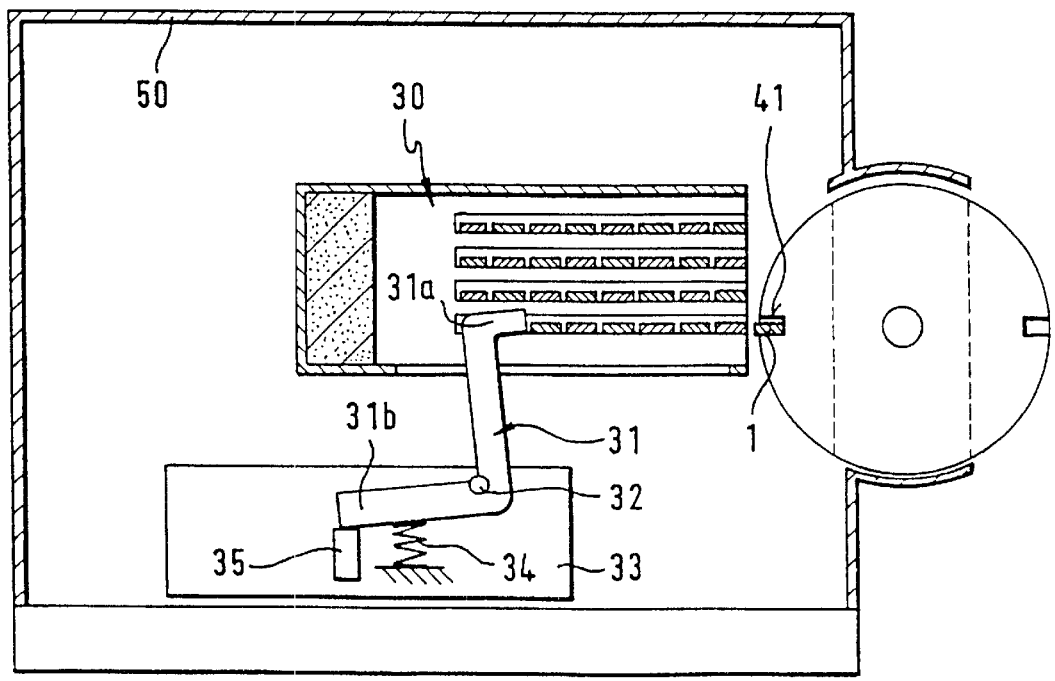
Figure 8C:
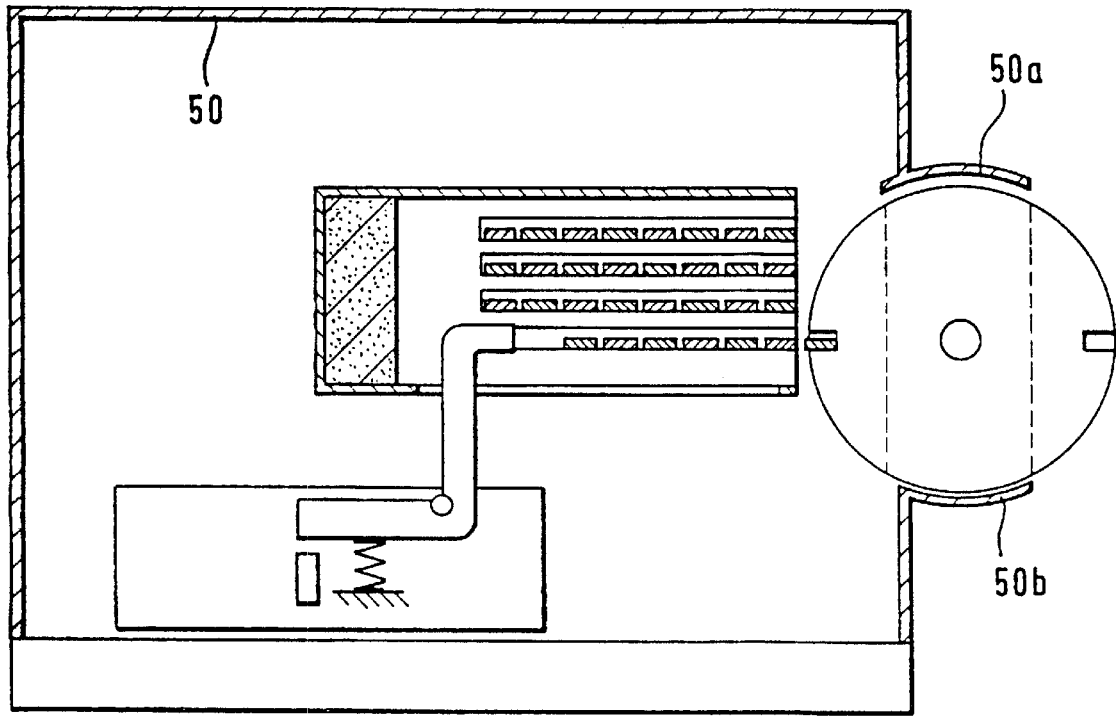
Figure 8D:
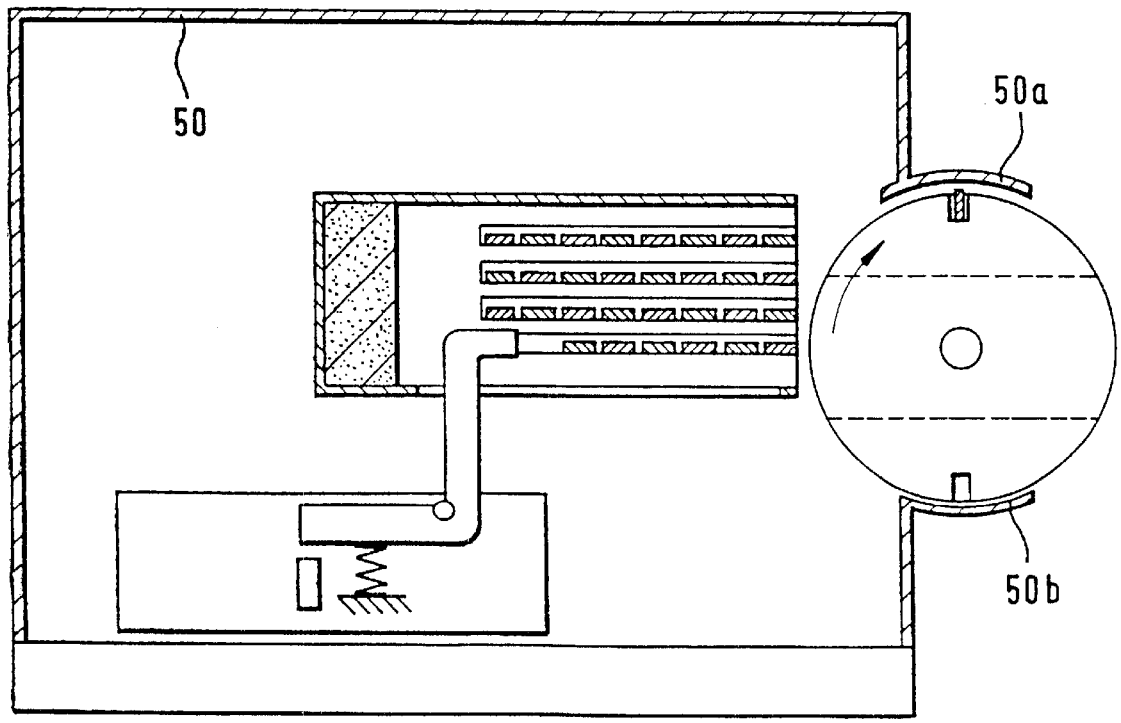

FIG. 8D shows how the test element located in the groove is transported through the gap between the protecting part (50a) and the roller by rotation of the roller. FIGS. 8C and 8D show that the test element protrudes slightly above the exterior contour of the roller. This corresponds to a preferred design in which the depth of the groove is less than the smallest expected test element width. This ensures that each test element protrudes at least slightly above the external contour of the roller and thus no subsequent test element can enter the groove together with the test element that is already located in the groove. Such a situation must be avoided since rotation of the roller would lead to a system failure as a result of jamming etc.. FIG. 8C also shows that the gap between the protecting parts (50a) and the roller is larger than the gap between the protecting part (50b) and the roller. In order to prevent test elements from falling out of the groove, the test element is transported through the upper gap. The gap between the protecting part (50b) and the roller can therefore be as small as the manufacturing tolerances allow.

Figure 8E:
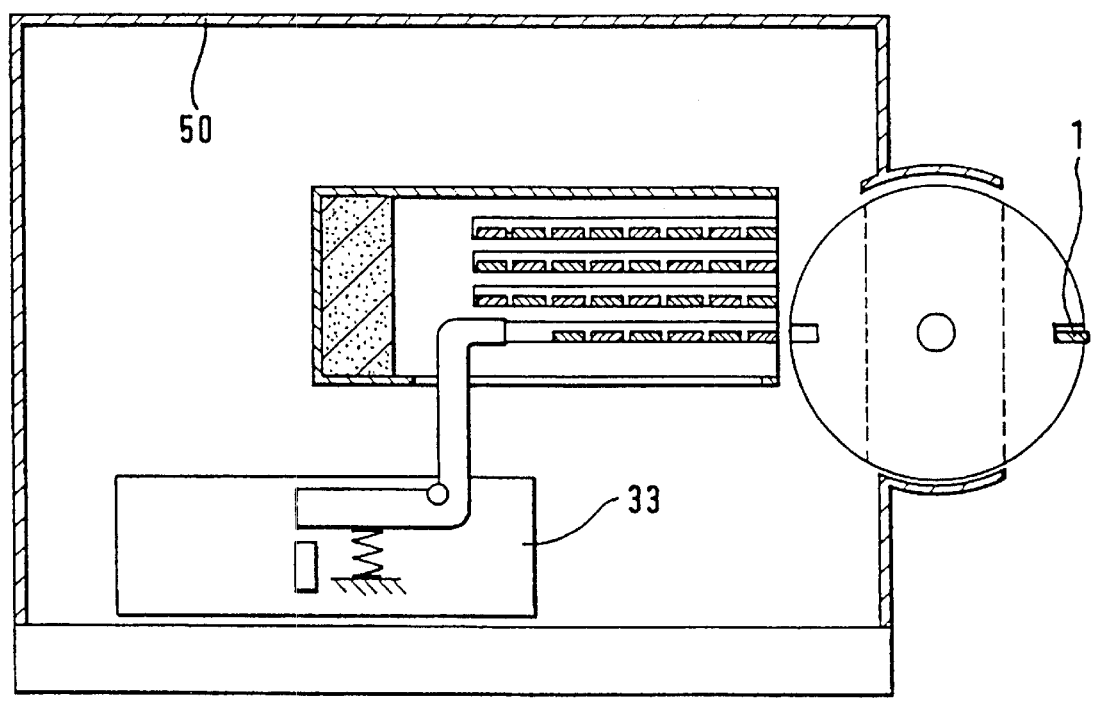

Usually the roller is rotated by 180° to remove a test element from the magazine which transports the test element into the position shown in FIG. 8E from which it can be collected with a gripping arm or such like.

Figure 9:
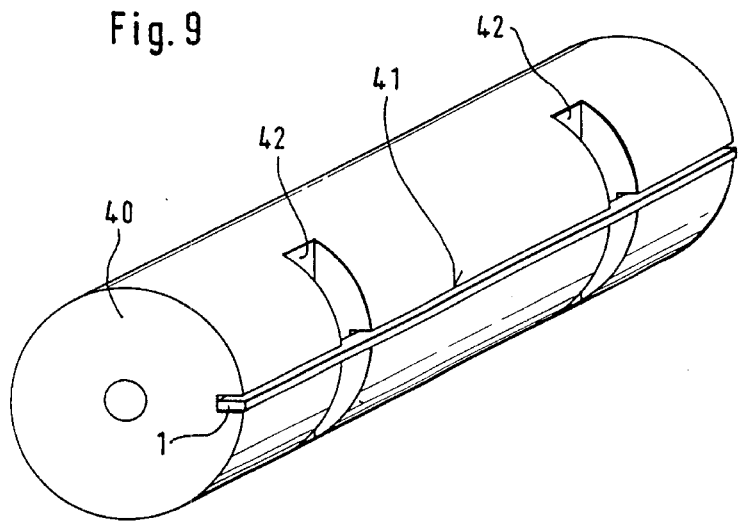

FIG. 9 shows a perspective view of the roller (40). A groove (41) is located in the roller which is integrated in the exterior peripheral surface of the roller and is parallel to the axis of the roller. A test element (1) is located in the groove. In order to remove the test element, the roller preferably has one or several slits (42) which are essentially perpendicular to the axis of the roller. The slits (42) extend starting from the surface of the roller towards the roller axis. The shape of the slits is preferably a "D". The slits are arranged in the area of the groove such that they undercut the groove and a space is made accessible in the area of the slits behind the test element which can be used to remove the test element.

Figure 10:
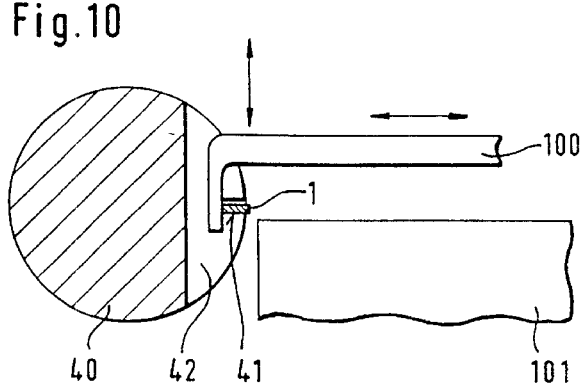

The roller shown in FIG. 9 is shown in cross-section in FIG. 10 together with a rake (100) for removal. The rake (100) can for example have the shape of a hook and be guided through the slit (42) behind the test element in order to remove the test element (1). The test element can be pulled out of the groove (41) onto a support (101) by a pulling movement of the rake. From here the test element can be subjected to further process steps in order to carry out an analysis.

Figure 11A:
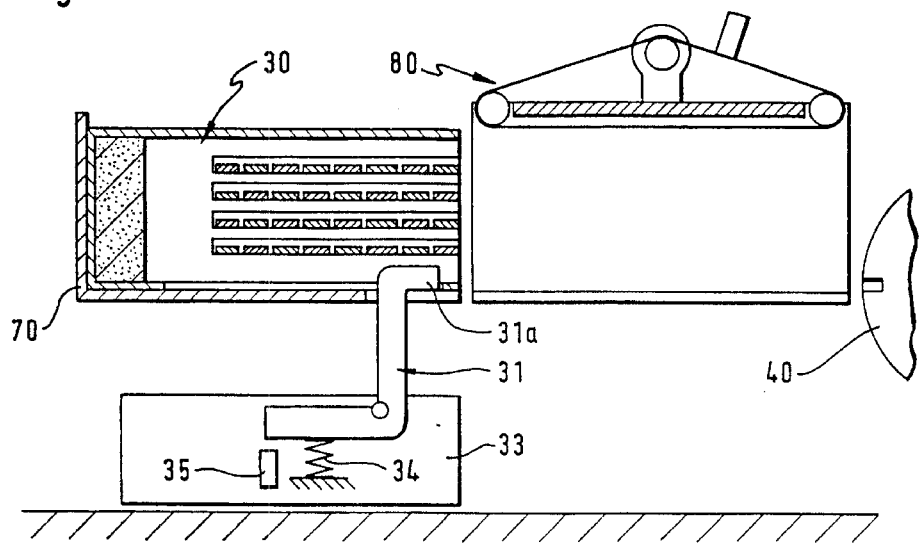

FIGS. 11A to F show a system for dispensing test elements which has a refill device for magazines. The system of FIG. 11 corresponds essentially to the system shown in FIG. 8 with regard to the function of the slide (31) and the roller (40). However, building on the system of FIG. 8 additional functions are possible with the system shown in FIG. 11. FIG. 11A shows a drawer (70) which can be pulled out and pushed into the system filled with a magazine (30). In order to remove test elements from the magazine, the magazine is moved into a removal position adjacent to the roller (40) (analogous to FIG. 8). For this purpose the system shown in FIG. 11A has a lifting platform (80) which can be moved vertically into which a magazine from the drawer can be inserted for which a separate device can be provided.

Figure 11B:
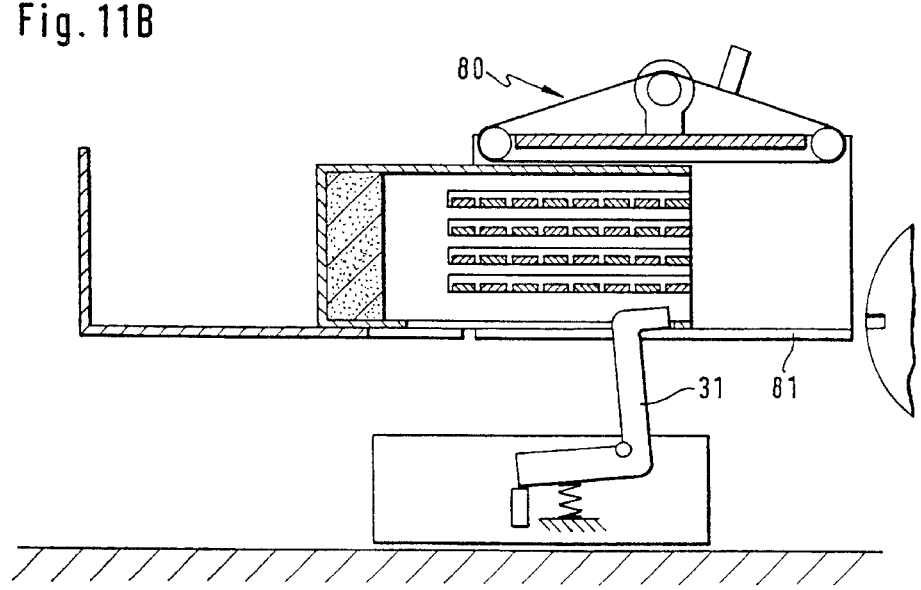
Figure 11E:
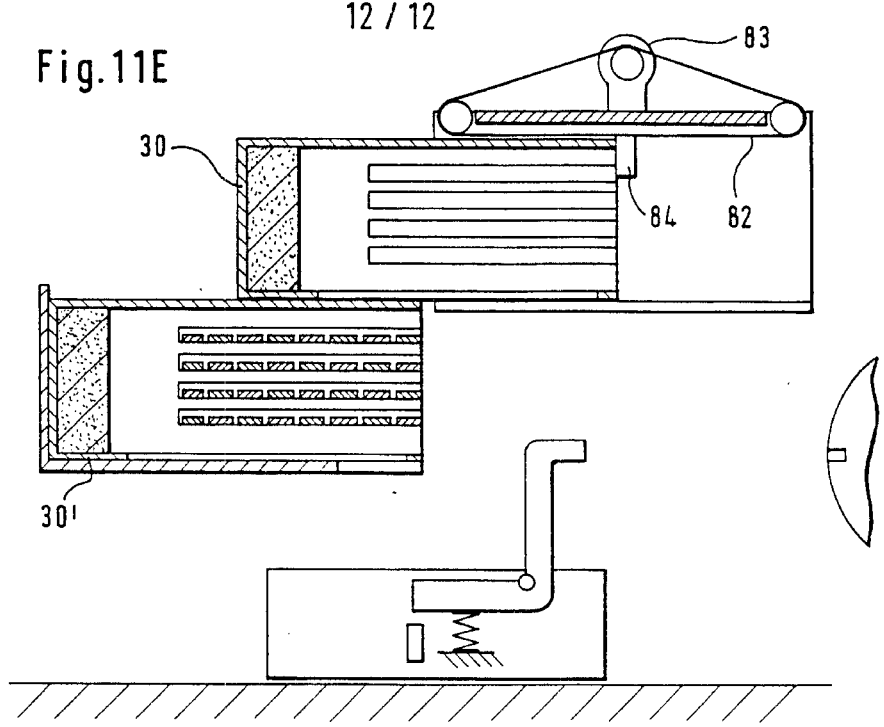

However, it is advantageous to use the slide (31) to move the magazine. For this purpose the moving carriage (33) is moved so far to the left that the slide (31) can engage from the underside into the magazine (30) located in the drawer (70). The moving carriage (33) is now moved towards the roller (40) so that the front end (31a) of the slide (31) catches on an edge of the magazine and pulls the magazine into the lifting platform as shown in FIG. 11B. The lifting platform (80) has a bottom surface (81) for receiving the magazine which prevents the magazine from falling down. The bottom surface (81) has a recess into which the slide (31) can be moved. When a magazine is completely inserted into the lifting platform (80), the test elements can be removed in a similar manner to that described for FIG. 8. It is also possible to fill the drawer which is now empty with a new magazine (30') as shown in FIG. 11C.

In order to remove test elements from the individual layers of the magazine, the magazine in the lifting platform can be moved vertically with the lifting platform (80) relative to the slide (31) and the roller (40). In each case they are removed from the layer located between the front end of the slide and the groove of the roller.

Figure 11F:
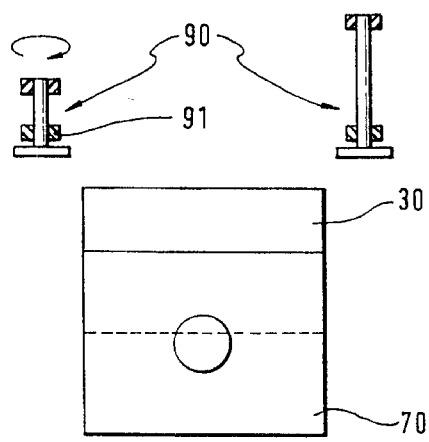

After a magazine in the lifting platform (80) has been emptied it can be simply replaced by a new magazine. For this the lifting platform (80) moves to a level at which the lower edge of the magazine (30) is located above the upper edge of the magazine (30') (see FIG. 11D). Now a mechanism which is part of the lifting platform is activated which slides the magazine (30) out of the lifting platform onto the magazine (30'). For this purpose the lifting platform can preferably have a circular belt (82) which is driven by a motor (83). An ejector cam (84) is attached to the belt which slides the magazine (30) as desired when the belt is moved. The magazine (30) can for example come to lie on the magazine (30') and falls into the drawer when the magazine (30') is pulled from under it according to FIG. 11B. However, the system of FIG. 11 preferably has the holding device shown as an example in 11F. When the magazine (30) is slid out from the lifting platform the magazine is firstly pushed into a holding device. Two opposing rollers (90) are shown in FIG. 11F between which the magazine (30) is pushed. The rollers (90) preferably have rubber overlays (91) or such like which make a close contact between the rollers and the magazine when the magazine (30) is inserted as a result of which the rollers rotate when the magazine is inserted and the magazine cannot fall in an uncontrolled manner. In order to lower the magazine into the drawer (70), the rollers (90) are moved apart to release the magazine. In FIG. 11F the position of the rollers is already shown in which the magazine is released. The described mechanism enables a controlled lowering of emptied magazines into the drawer without jamming.

The emptied magazine which is now located in the drawer can be removed by the operator and optionally replaced by a fresh magazine. Hence a continuous operation is possible with this system which only seldomly requires an action by the user.

List of reference numerals

| | |
|---|---|
| (1) | test element |
| (2) | support |
| (3) | test zone |
| (10a) | left side face |
| (10b) | right side face |

-continued

List of reference numerals

| | |
|---|---|
| (11) | desiccant chamber |
| (12) | front side |
| (13) | arrow in the feed direction |
| (14) | ejector slide |
| (15) | arrow in the ejection direction |
| (16a, 16b) | slits |
| (17) | slide |
| (18a, 18b) | pair of grooves |
| (20) | individual frame |
| (21) | edge |
| (22) | ledge |
| (23) | rectangular recess |
| (24) | slit |
| (30) | magazine |
| (31) | slide |
| (31a) | front end of the slide |
| (31b) | rear end of the slide |
| (32) | axis |
| (33) | sliding carriage |
| (34) | spring |
| (40) | sensor |
| (40) | roller |
| (41) | groove |
| (42) | slit |
| (50) | housing |
| (60) | desiccant |
| (70) | drawer |
| (80) | lifting platform |
| (81) | bottom of the lifting platform |
| (82) | belt |
| (83) | motor |
| (84) | ejector cam |
| (90) | rollers |
| (91) | rubber overlay |
| (100) | rake |
| (101) | support |

What is claimed is:

1. A magazine for storing test elements having at least one test zone disposed on a support, wherein the magazine comprises at least a pair of side walls comprising opposing guide grooves in which the test elements can be inserted in such a way that they lie adjacent to one another and edges of adjacent supports of the test elements abut one another.

2. The magazine of claim 1 wherein the magazine comprises at least two pairs of said opposing guide grooves and the pairs are arranged above one another.

3. The magazine of claim 2 wherein the guide grooves are integrated into a said side wall of the magazing and at least one opening per pair of guide grooves is located in a side wall of the magazine.

4. The magazine of claim 3 wherein the opening has a rectangular cross-section, its height is 10 to 50% larger than the maximum height of the test elements and its width is 10 to 50% larger than the width of the test elements.

5. The magazine of claim 3 further comprising a front face which is essentially perpendicular to the side walls of the magazine.

6. The magazine of claim 5 wherein there is either one opening per pair of grooves in the front face which is located such that test elements which are moved in the grooves can emerge from the magazine through the opening or the front face is open.

7. The magazine of claim 6 wherein the opening has a rectangular cross-section, its width is 10 to 30% larger than the maximum height of the test elements and its length is 0.5 to 20% larger than the length of the test strips.

8. The magazine of claim 6 further comprising spring elements which move the test elements within the grooves so that a test element can be moved to a position near the opening and removed through the opening.

9. The magazine of claim 1 wherein the magazine comprises walls which enclose the magazine.

10. The magazine of claim 9 further comprising at least one cut-out in a wall which is parallel to the plane of test elements.

11. The magazine of claim 1 further comprising a desiccant in the interior of the magazine.

12. The magazine of claim 1 wherein the front side of the magazine is at least partially sealed by a sealing foil.

13. The magazine of claim 12 wherein the rear side of the magazine is sealed by a desiccant chamber.

14. The magazine of claim 1 wherein the magazine comprises:

(a) two side walls with integrated guide grooves;

(b) two walls which link the side walls together in such a way that the magazine has a cubical shape; and (c) a desiccant chamber which is located at a rear side of the magazine.

15. The magazine of claim 14 wherein the open end face of the magazine is at least partially closed by a sealing foil.

16. The magazine of claim 14 wherein the magazine is injection molded as an integral unit and comprises film hinges that join the walls of the magazine together.

* * * * *